(12) United States Patent
Williams et al.

(10) Patent No.: US 8,709,018 B2
(45) Date of Patent: Apr. 29, 2014

(54) NON-BALLOON LOW PROFILE FEED DEVICE WITH INSERTION/REMOVAL TOOL

(75) Inventors: Derek M. Williams, Cuyahoga Falls, OH (US); Grant W. Phillips, Bedford, OH (US)

(73) Assignee: Applied Medical Technology, Inc., Garfield Heights, OH (US)

( * ) Notice: Subject to any disclaimer, the term of this patent is extended or adjusted under 35 U.S.C. 154(b) by 1345 days.

(21) Appl. No.: 11/531,946

(22) Filed: Sep. 14, 2006

(65) Prior Publication Data
US 2007/0078465 A1 Apr. 5, 2007

Related U.S. Application Data

(60) Provisional application No. 60/717,840, filed on Sep. 16, 2005.

(51) Int. Cl.
*A61F 11/00* (2006.01)
*A61M 5/178* (2006.01)
*A61M 5/32* (2006.01)

(52) U.S. Cl.
USPC ............... 606/108; 604/165.02; 604/170.03; 604/174

(58) Field of Classification Search
USPC ........... 606/108; 604/164.03, 165.01–165.02, 604/170.01–170.02, 170.03, 174
See application file for complete search history.

(56) References Cited

U.S. PATENT DOCUMENTS

| 4,863,438 A | 9/1989 | Gauderer et al. |
| 5,336,203 A | 8/1994 | Goldhardt et al. |
| 5,429,598 A | 7/1995 | Waxman et al. |
| 5,454,821 A * | 10/1995 | Harm et al. ............... 606/148 |
| 5,935,107 A | 8/1999 | Taylor et al. |
| 5,989,225 A * | 11/1999 | Bodicky et al. ............ 604/174 |
| 2003/0208100 A1 | 11/2003 | Levy |
| 2005/0251150 A1 | 11/2005 | Hirano |
| 2008/0208208 A1 * | 8/2008 | Nagata et al. ............. 606/108 |

FOREIGN PATENT DOCUMENTS

| EP | 0 824 929 A2 | 2/1998 |
| EP | 1 334 744 A2 | 8/2003 |
| JP | H7-16235 A | 1/1995 |

(Continued)

OTHER PUBLICATIONS

International Search Report, Jan. 10, 2008.

(Continued)

*Primary Examiner* — Katherine Dowe
*Assistant Examiner* — Michael Mendoza
(74) *Attorney, Agent, or Firm* — Pearne & Gordon LLP

(57) ABSTRACT

A device for inserting a non-balloon gastrostomic device through an opening in the wall of the abdomen and stomach or other viscera of a patient is provided. The insertion device comprises a body, a stylus, and a trigger device being adapted to selectively maintain a selected position of the stylus relative to the body without the use of an external force. A method of inserting the gastrostomic device utilizing the insertion tool is also provided. In addition or alternatively, a gastrostomic device is provided including a hollow tube member and an enlarged resiliently deformable tip at one end of the tube member. The deformable tip is deformable between a first configuration and a second configuration, each configuration having a cross-sectional area. In addition or alternatively, a method is provided for forming the gastrostomic device using a disposable core.

20 Claims, 10 Drawing Sheets

(56) References Cited

FOREIGN PATENT DOCUMENTS

| | | |
|---|---|---|
| JP | H9-511934 T | 12/1997 |
| JP | H9-512732 T | 12/1997 |
| JP | 2000-507134 A | 6/2000 |
| JP | 2005-168980 A | 6/2005 |
| WO | 95/28200 A1 | 10/1995 |
| WO | 95/30449 A1 | 11/1995 |
| WO | 97/34552 A1 | 9/1997 |
| WO | 2004/096115 A1 | 11/2004 |
| WO | 2005/105018 A1 | 11/2005 |

OTHER PUBLICATIONS

European Search Report dated Sep. 24, 2009.
Notice of Rejection issued in corresponding Japanese patent application No. 2008-531375 on Apr. 26, 2011.
Notice of Rejection issued in corresponding Japanese patent application No. 2008-531375 on Apr. 4, 2012.

* cited by examiner

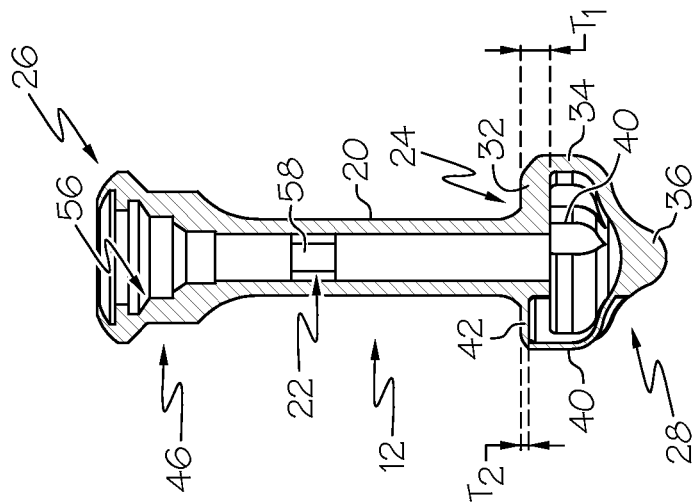
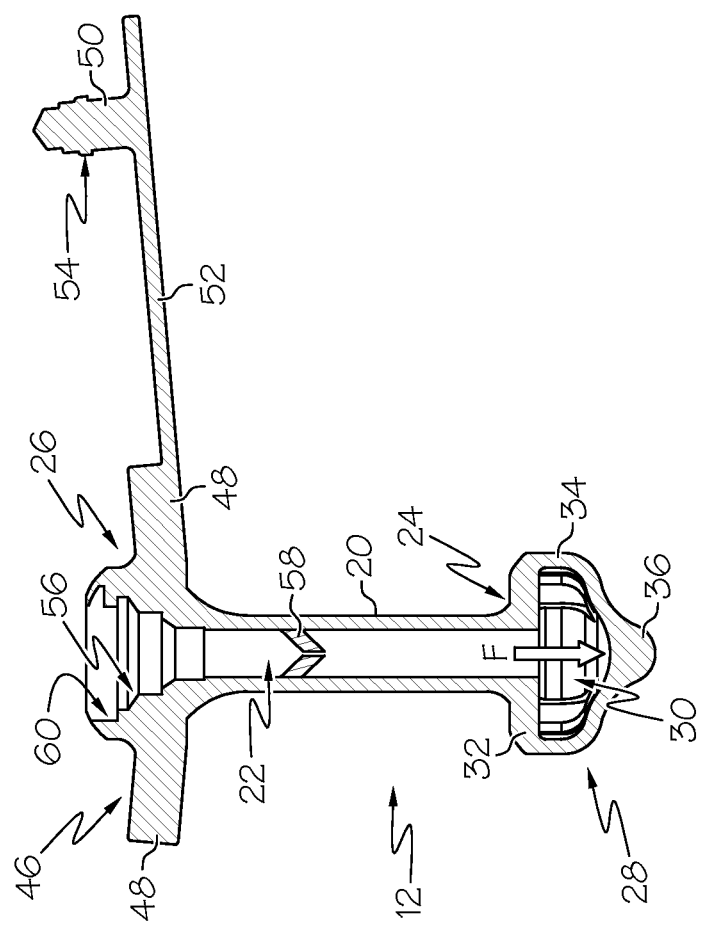

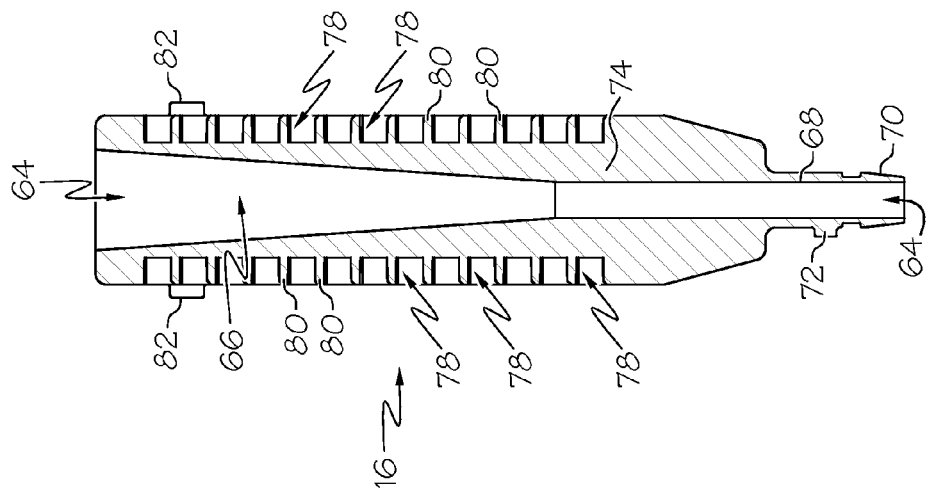
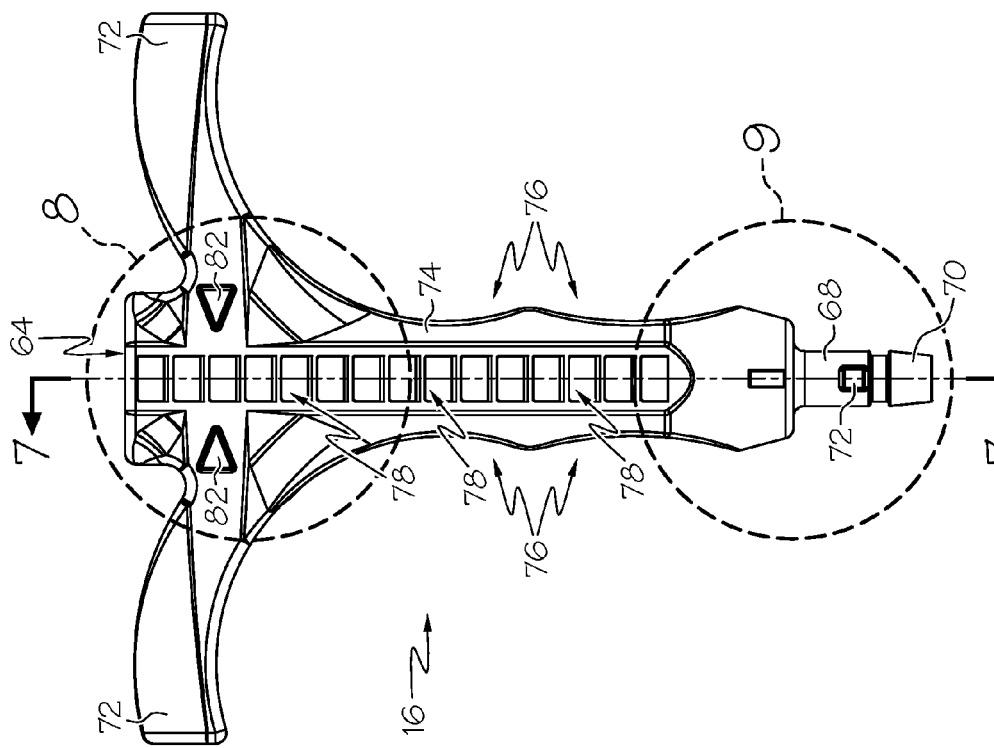

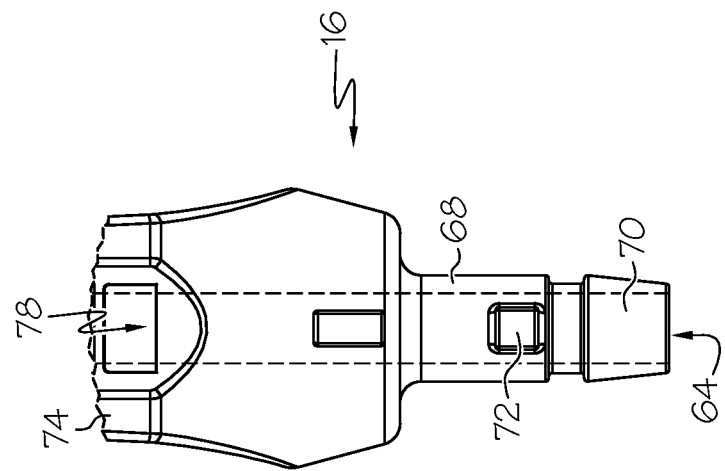
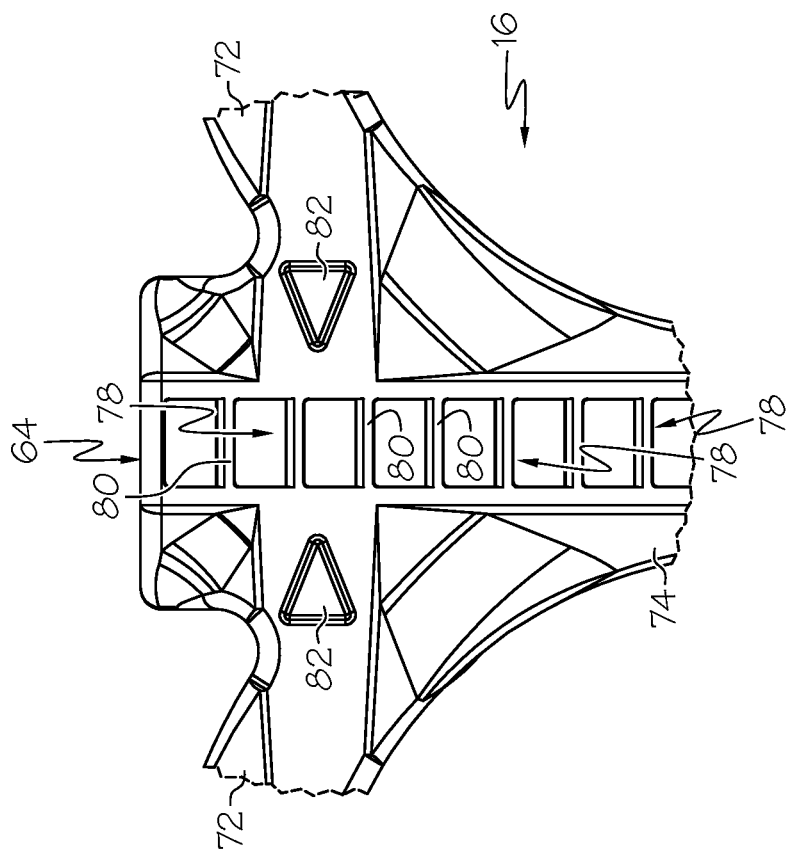

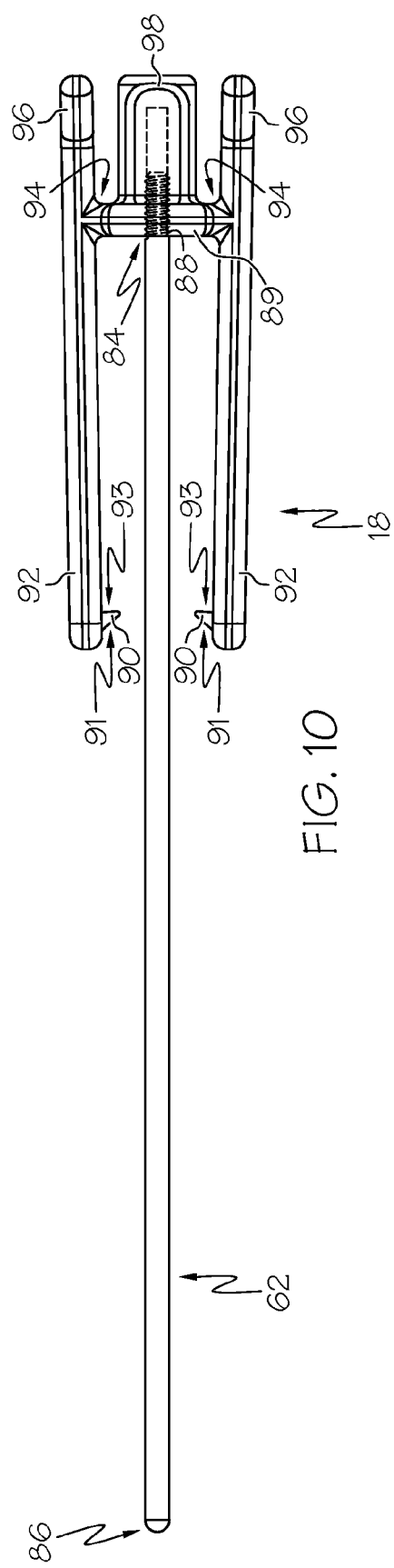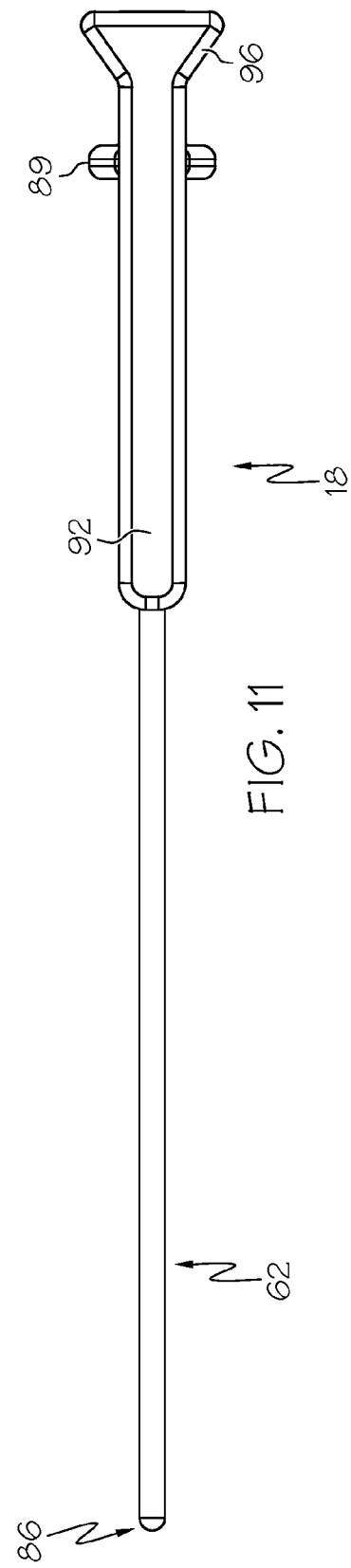

NON-BALLOON LOW PROFILE FEED DEVICE WITH INSERTION/REMOVAL TOOL

RELATED APPLICATIONS

This application claims the benefit of U.S. Provisional Application No. 60/717,840, filed on Sep. 16, 2005, the entire disclosure of which is hereby incorporated herein by reference.

FIELD OF THE INVENTION

The present invention relates to gastrostomy devices, and more particularly, to systems and methods for insertion and removal of non-balloon gastrostomy devices.

BACKGROUND OF THE INVENTION

Low profile gastrostomy devices are designed to be inserted through an opening in the wall of the abdomen and stomach of a patient for use in supplying nutrients and other fluids, including medication, into the stomach. Such devices can also be used for decompression, and provides access for examination endoscopically, for example, using fiber optics. Other uses requiring insertion of a tube into other viscera of the body may be made of the device, such as urinary bladder drainage, ileostomy, jejunostomy, and cystostomy.

Certain medical conditions require the long-term access for such purposes as internal feedings and/or medication to a person's stomach or other viscera of the body. This may be accomplished be inserting a tube through a surgical opening into the stomach or other viscera.

Problems with conventional gastrostomy tubes are common in both adults and children. These range from stomal irritation to more serious mishaps. Accidental removal and internal migration are also oftentimes encountered with conventional gastrostomy tubes.

Current non-balloon devices are inserted with an obturator rod that elongates it prior to insertion. Most of these must be held elongated manually by the end user. This makes it more difficult to manipulate the device during insertion, and more often the device is simply shoved through the stoma site. Additionally, current devices lack a method to aid in removal. They are simply traction removed, without reducing the cross-sectional area by any means prior to removal. The low profile gastrostomy feeding device of the present invention solves these issues by elongating and maintaining the device, which can then be inserted with careful manipulation using the thumb and forefinger into an existing stoma site. Removal is similar to insertion, as the device can be elongated blindly using a ratcheted scale corresponding to the size and length of the device that is in place.

BRIEF SUMMARY OF THE INVENTION

The following presents a simplified summary of the invention in order to provide a basic understanding of some aspects of the invention. This summary is not an extensive overview of the invention. It is intended to identify neither key nor critical elements of the invention nor delineate the scope of the invention. Its sole purpose is to present some concepts of the invention in a simplified form as a prelude to the more detailed description that is presented later.

In accordance with an aspect of the present invention, a device for inserting a non-balloon gastrostomic device through an opening in the wall of the abdomen and stomach or other viscera of a patient is provided. The device comprises a body including an aperture extending therethrough and an attachment member configured to removably attach the body to a gastrostomic device. The device further includes a stylus having a proximal end and a terminal end, the terminal end being configured to extend a distance through the aperture of the body to deform a portion of a gastrostomic device attached to the body. The device further includes a trigger device attached to the proximal end of the stylus and being adapted to selectively maintain a selected position of the terminal end of the stylus relative to the body without the use of an external force.

In accordance with another aspect of the present invention, a method of inserting a non-balloon gastrostomic device through an opening in the wall of the abdomen and stomach or other viscera of a patient is provided. The method comprises the steps of providing a gastrostomic device including a hollow tube member having an inner end and an outer end, a longitudinal passage extending completely through the tube member from one end to the other, and an enlarged resiliently deformable tip at the inner end of the tube member. The deformable tip is deformable between a first configuration having a first cross-sectional area and a second configuration having a second cross-sectional area, the second cross-sectional area being less than the first cross-sectional area. The method also includes the step of providing an insertion device being adapted to deform the deformable tip of the gastrostomic device into each of the first configuration and the second configuration, and being further configured to selectively maintain the deformable tip in the second configuration without the use of an external force. The method further includes the steps of removably attaching the insertion device to the outer end of the gastrostomic device, utilizing the insertion device to deform the deformable tip of the gastrostomic device into the second configuration, and utilizing the insertion device to maintain the deformable tip of the gastrostomic device in the second configuration without the use of an external force. The device further includes the steps of inserting the deformable tip of the gastrostomic device through an opening in the wall of the abdomen and stomach or other viscera of a patient until the outer end of the gastrostomic device is adjacent the abdomen of a patient, utilizing the insertion device to permit the deformable tip of the gastrostomic device to resiliently return to the first configuration, and detaching the insertion device from the outer end of the gastrostomic device.

In accordance with another aspect of the present invention, a non-balloon gastrostomic device for insertion through an opening in the wall of the abdomen and stomach or other viscera of a patient is provided. The device includes a hollow tube member having an inner end, an outer end, and a longitudinal passage extending completely through the tube member from one end to the other, and an enlarged resiliently deformable tip at the inner end of the tube member. The deformable tip is hollow and includes an end wall surrounding the inner end of the tube member, the end wall having a first thickness, and an outer cap portion attached to the end wall. The deformable tip is deformable between a first configuration wherein the end wall has a first cross-sectional area and a second configuration wherein the end wall has a second cross-sectional area, the second cross-sectional area being less than the first cross-sectional area. The device further includes an aperture formed through the outer cap portion, the aperture permitting the passage of fluid entering the deformable tip from the tube member, and a strap disposed within the aperture and connected between the outer cap portion and a portion of the end wall. The associated portion of the end wall attached to the strap has a second thickness, the second thickness being less than the first thickness.

In accordance with another aspect of the present invention, a method of forming a non-balloon gastrostomic device for insertion through an opening in the wall of the abdomen and stomach or other viscera of a patient is provided. The method can be utilized with a gastrostomic device including a hollow tube member having an inner end and an outer end, a longitudinal passage extending completely through the tube member from one end to the other, and an enlarged tip at the inner end of the tube member, the enlarged tip having a hollow interior. The method includes the steps of providing a core having a geometry generally equal to an interior geometry of the hollow enlarged tip, forming the gastrostomic device around the core, and disposing of the core from the gastrostomic device to form the hollow enlarged tip.

BRIEF DESCRIPTION OF THE DRAWINGS

The foregoing and other features and advantages of the present invention will become apparent to those skilled in the art to which the present invention relates upon reading the following description with reference to the accompanying drawings, in which:

FIG. 4 illustrates a sectional view along line 4-4 of FIG. 2;

FIG. 5 illustrates a sectional view along line 5-5 of FIG. 3;

FIG. 6 illustrates a front view of an example body of the insertion tool in accordance with another aspect of the present invention;

FIG. 7 is similar to FIG. 6, but illustrates a sectional view along line 7-7 of FIG. 6;

FIG. 8 is similar to FIG. 6, but illustrates a detail view of section 8 of FIG. 6;

FIG. 9 is similar to FIG. 6, but illustrates a detail view of section 9 of FIG. 6;

FIG. 10 illustrates a top view of an example trigger device and stylus according to another aspect of the present invention;

FIG. 11 is similar to FIG. 10, but illustrates a side view;

DESCRIPTION OF EXAMPLE EMBODIMENTS

Figure 1:
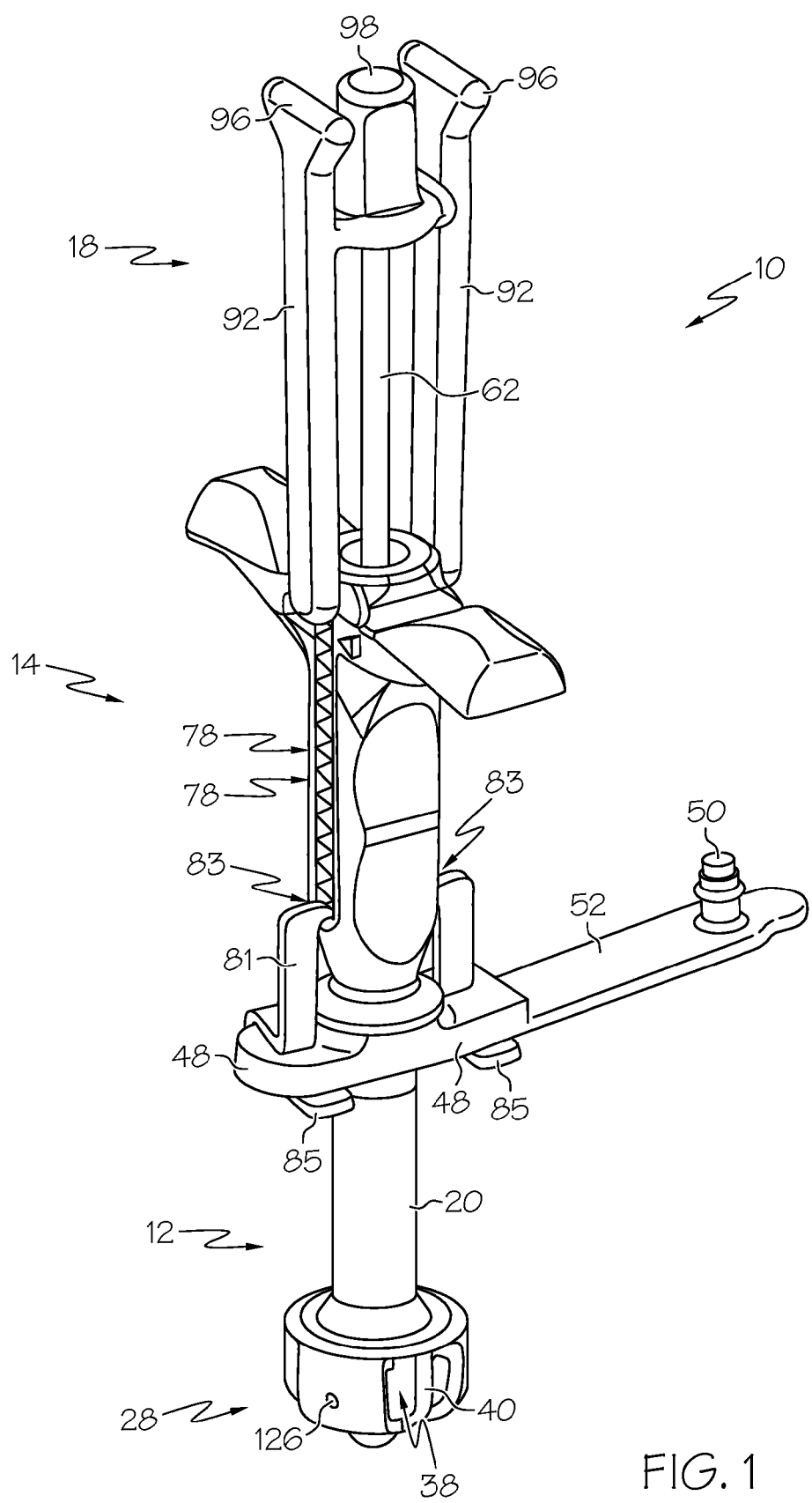
FIG. 1 illustrates a perspective view of an example non-balloon gastrostomic device with an insertion/removal tool in accordance with an aspect of the present invention.

An example embodiment of a device that incorporates aspects of the present invention is shown in the drawings. It is to be appreciated that the shown example is not intended to be a limitation on the present invention. For example, one or more aspects of the present invention can be utilized in other embodiments and even other types of devices.

Turning to the shown example of FIG. 1, an example non-balloon, low-profile gastrostomy feeding device 10 is illustrated in accordance with an aspect of the present invention. The low profile gastrostomy feeding device 10 includes a non-balloon, low profile gastrostomic device 12 for insertion through an opening in the wall of the abdomen and stomach (e.g., an existing stoma), or other viscera of a patient (e.g., bladder, chest, colon, etc.) for various procedures (e.g., ileostomy, jejunostomy, cystostomy, etc.). The gastrostomic device 12 is coupled to an insertion/removal device 14, which comprises a body portion 16 and a trigger device 18. The low-profile gastrostomy feeding device 10 is adapted to ease pain associated with insertion and removal of a non-balloon gastrostomic device 12. More specifically, a cross-sectional area of the device is reduced when it is elongated, as will be described in further detail below. Additionally, the low profile gastrostomy feeding device 10 is adapted to facilitate articulation of the gastrostomy device into an existing stoma site.

Turning now to FIGS. 2-5, an example non-balloon gastrostomic device 12 is illustrated in greater detail in accordance with an aspect of the present invention. The gastrostomic device 12 is generally a flexible, one-piece device including an elastomeric material, though the device can comprise a multi-piece device and/or include various other materials. In one example, the gastrostomic device 12 can be formed of a biocompatible long-lasting resiliently deformable material, such as medical grade silicone rubber. The gastrostomic device 12 can include a hollow tube member 20 of a length long enough to extend through an opening in an abdominal wall and stomach wall of a patient (e.g., see FIGS. 12d-12g). A longitudinal passage 22 extends completely through the tube member 20 from one end to the other. It is to be appreciated that various portions of the longitudinal passage 22 can include various diameters and/or cross-sectional geometries, though as shown in FIGS. 4-5, a central portion of the passage 22 can include a single diameter. Additionally, the hollow tube member 20 can include an inner end 24 and an outer end 26, as will be discussed more fully herein.

The gastrostomic device 12 can further include an enlarged, resiliently deformable tip 28 disposed at the inner end 24 of the tube member 20. As shown in FIG. 4-5, the deformable tip 28 can have a mushroom shape and can have a generally hollow interior 30. The hollow interior 30 is in fluid communication with the longitudinal passage 22 for the delivery or extraction of fluids, such as food and/or medicine, to the patient, as will be described more fully herein. The deformable tip 30 can include an end wall 32 surrounding the inner end 24 of the tube member 20. As shown, the end wall 32 can have a generally circular cross-section, though it is to be appreciated that it can also have various other cross-sectional geometries, such as triangular, square, polygonal, etc. Additionally, the deformable tip 28 can include various sizes for use with various patients, such as common French sizes 12, 14, 16, 18, 20, 22, 24, 28, etc. Further, as shown in FIG. 5, the end wall 32 can have a first thickness $T_1$.

Figure 12A:
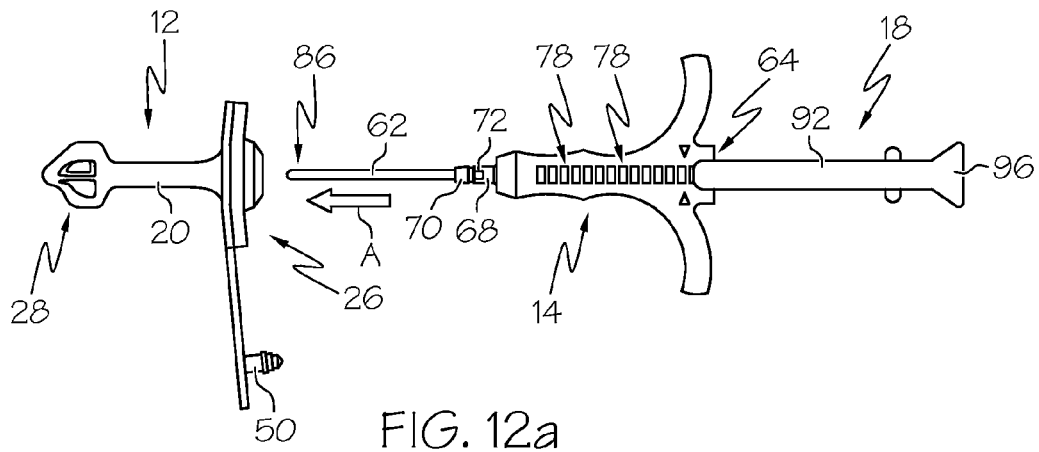
FIGS. 12a-12g illustrate the steps of an example method of inserting an example non-balloon gastrostomic device into a patient in accordance with an aspect of the present invention.
Figure 12B:
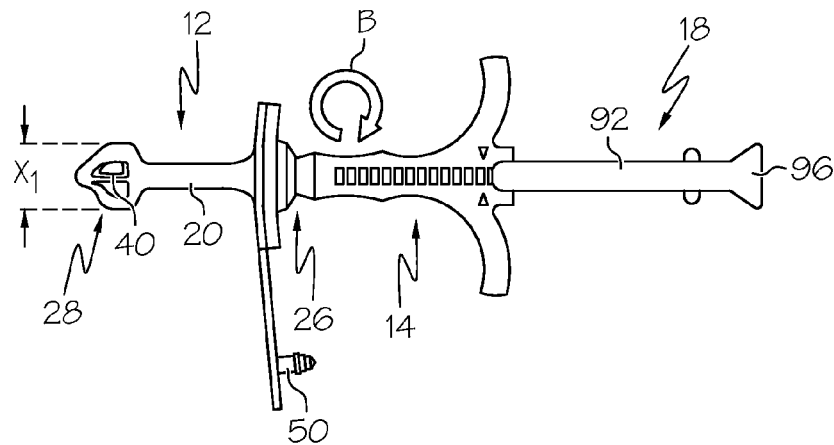
Figure 12C:
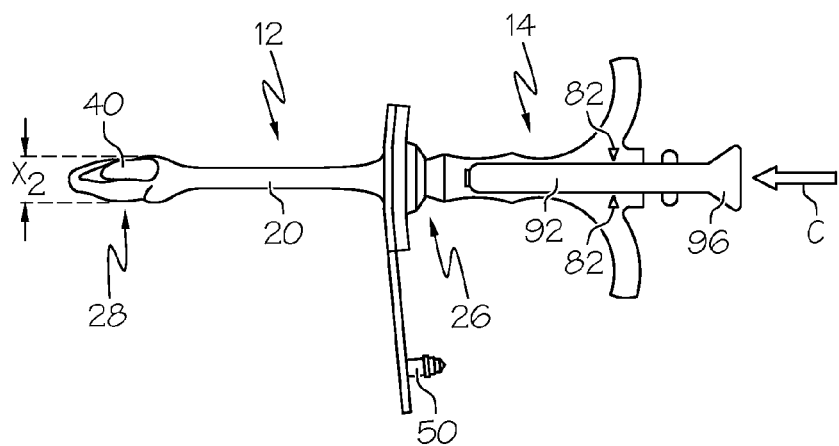

Turning briefly to the examples shown in FIGS. 12b and 12c, the deformable tip 28 can be elongated and deformed between at least a first configuration and a second configuration. In the first configuration, as shown in FIG. 12b, the end wall 32 has a first cross-sectional area $X_1$, and in the second configuration, as shown in FIG. 12c, a second configuration wherein the end wall 32 has a second cross-sectional area $X_2$. As shown, the second cross-sectional area $X_2$ is less than the first cross-sectional area $X_1$ to facilitate insertion and removal of the gastrostomic device 12 from the patient. It is to be appreciated that the deformable tip 28 can also be deformed among a plurality of configurations (e.g., three or more), each of the plurality of configurations being associated with a cross-sectional area of the end wall 32. Thus, the gastrostomic device 12 can be customizable to the needs of each individual patient and/or situation.

The deformable tip 30 can further include an outer cap portion 34 attached to the end wall 32. As shown, the outer cap portion 34 can be formed with the end wall 32, though it can also be attached thereto by various methods, such as adhesives, welding, etc. Similar to the end wall 32, the outer cap portion 34 can have a generally circular cross-section, or various other cross-sectional geometries (e.g., triangular, square, polygonal, etc.). Additionally, the outer cap portion 34 can further include an apex 36 at a terminal end thereof. It is to be appreciated that the apex 36 can include more than the tip of the outer cap portion 34, and may include the generally thickened area adjacent the tip. Generally, application of an external force (e.g., a force supplied by a user) to a portion of the apex 36 can cause the deformable tip 28 to be deformed between the first and second configurations. Specifically, as shown in FIG. 4, application of the external force F to the apex 36 can cause an elongation of the deformable tip 28 to form a desired cross-sectional area of the end wall 32. It is to be appreciated that the apex 36 can include a thickened portion having a greater amount of material (e.g., a greater thickness of silicone) to enable it to withstand application of the external force F without damage or degradation of the gastrostomic device 12.

Figure 3:
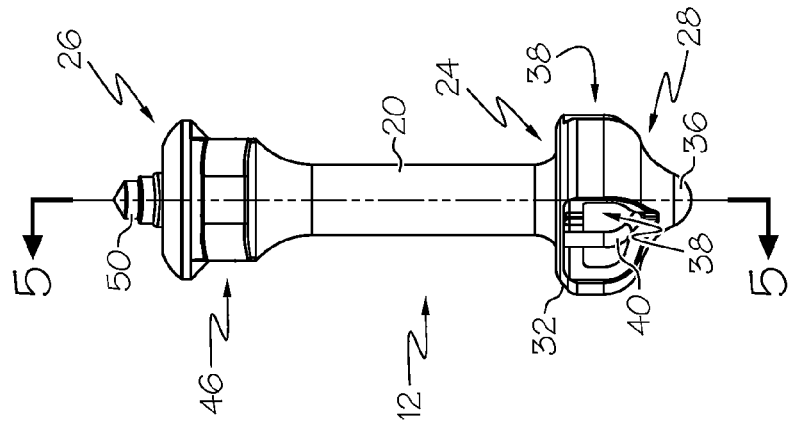
FIG. 3 is similar to FIG. 2, but illustrates a side view of the non-balloon gastrostomic device.
Figure 2:
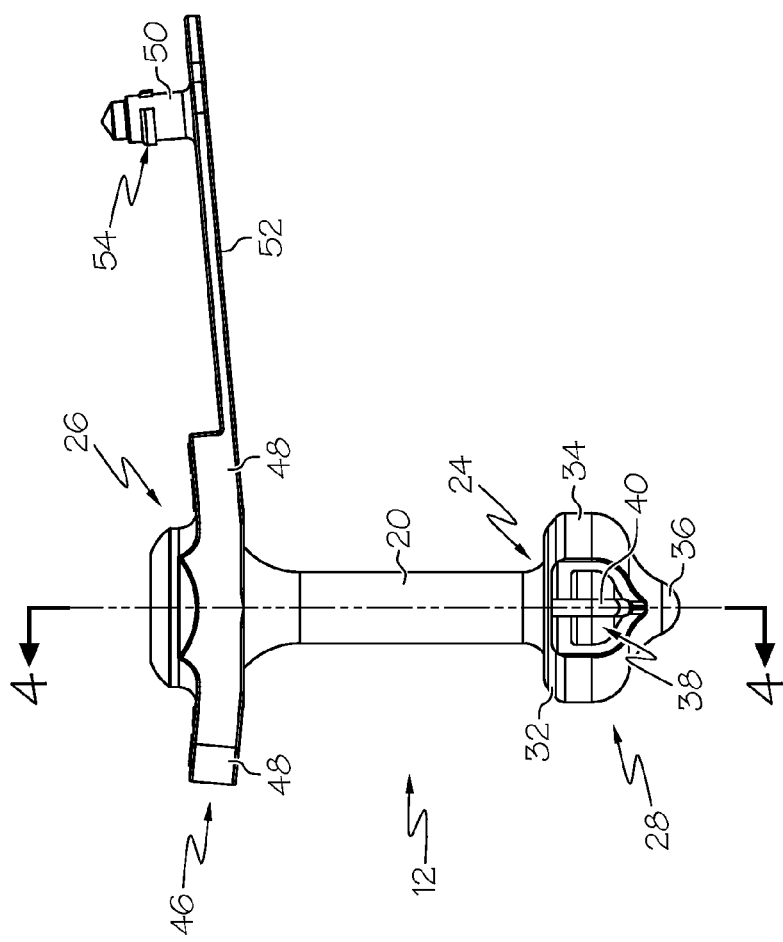
FIG. 2 illustrates a front view of an example non-balloon gastrostomic device in accordance with an aspect of the present invention.

Turning back to the examples shown in FIG. 2-3, the gastrostomic device 12 can include an aperture 38 formed through the outer cap portion 34. Because the hollow interior 30 of the deformable tip 28 is in fluid communication with the longitudinal passage 22 for the delivery of fluids, the aperture 38 can permit the passage of fluid entering the deformable tip 28 into or out of the stomach or other internal portion of a patient. The gastrostomic device 12 can include a plurality of apertures 38. For example, as shown in the various figures, the gastrostomic device 12 can include three apertures 38 symmetrically arranged about the deformable tip 28, though various other numbers of apertures 38 can also arranged in various patterns, or even randomly. Further, as shown, the apertures 38 can generally follow the geometry of the deformable tip 28, though they can also include various other geometries.

The gastrostomic device 12 can further include a strap 40 disposed within the aperture 38 and connected between the outer cap portion 34 and a portion of the end wall 32. As shown, each strap 40 can be attached to the outer cap portion 34 adjacent the apex 36. The strap 40 can be formed with outer cap portion 34 and the end wall 34, though it can also be attached thereto by various methods, such as adhesives, welding, fasteners, etc. As can be appreciated, the gastrostomic device 12 can include a plurality of straps 40 arranged variously. In the shown figures, each aperture 38 includes a single strap 40, though various numbers of straps can be included for each aperture 38.

The strap 40 can be attached to a portion 42 of the end wall 32 having a thickness different than the first thickness $T_1$ to facilitate deformation of the deformable tip 28. As shown in FIG. 5, the associated portion 42 of the end wall 32 attached to the strap 40 can have a second thickness $T_2$ that is less than the first thickness $T_1$. Additionally, each portion 42 of the end wall 32 having the second thickness $T_2$ can include various geometries, such as a triangular geometry 44, as shown schematically in FIG. 13a on a component that can be used during a forming process. Thus, because each strap 40 can be attached to the outer cap portion 34 adjacent the apex 36, application of the external force F to the apex 36 is transmitted through the strap 40 to the associated portion 42 of the end wall 32. Additionally, because the associated portion 42 has a lesser thickness $T_2$, the straps 40 can cause the associated portions 42 to deform inwardly during elongation of the deformable tip 28. Additionally, because of the lesser thickness $T_2$, the associated portions 42 can deform more than the other portions of the end wall 32. Thus, the deformation of the associated portions 42 can facilitate a generally uniform, streamlined, elongated geometry of the deformable tip 28 that permits a greater cross-sectional area reduction.

The gastrostomic device can further include a flange member 46 integrally molded on the outer end 26 of the tube member 20. The flange member 46 can further include a pair of diametrically oppositely extending, relatively short, substantially flat wings 48. The wings are configured to lie generally flush with an outside abdominal wall of a patient. The wings 48 are preferably relatively narrow in width, whereby if irritation of the skin should occur in the area of the wings 48, the tube portion 20 can readily be rotated a part turn so that the wings 48 overlie different non-irritated areas of the skin. The axial distance between the opposed surfaces of the deformable tip 28 and the flange member 46 (e.g., including the wings 48) generally corresponds to a distance between an inside wall of a patient's stomach and the outer abdominal wall of a patient. Thus, the flat wings 48, along with the deformable tip 28, can make the device self-retaining in the patient when the deformable tip 28 has expanded against an inside wall of the stomach and the wings 48 are generally flush with an outside abdominal wall. In one example, although the dimensions of the device may vary somewhat, it has been found that three different sizes, each having substantially the same dimensions except for the length of the tube member 20 itself, may be used with a majority of patients. The smaller size desirably has a tube length extending between the opposed surfaces of the deformable tip 28 and wings 48 at opposite ends of the tube of approximately 0.590 inch for use with small patients, the intermediate size desirably has a tube length of approximately 1.1 inch for use with medium size patients, and the larger size desirably has a tube length of approximately 1.7 inch for larger patients, though it is to be appreciated that various other sizes can also be used.

The gastrostomic device 12 can further include various other features. For example, a plug 50 can be integrally connected to the outer end of one of the wings 48 by a flexible membrane 52 which permits the plug 50 to be inserted into the axial outer end 26 of the passage 22 in the tube member 20 to completely close off such passage 22, and to be removed therefrom as desired without fear of losing or misplacing the plug 50. Though the plug 50 is shown tethered to the gastrostomic device 12 by the flexible membrane 52, a loose and untethered plug 50 can also be used. Details of an interaction between the plug 50 and the outer end 26 of passage 22 are illustrated with respect to FIGS. 4-5. Specifically, the plug 50 can include one or more annular rings 54 configured for sealing engagement with one or more annular recesses 56 (e.g., forming shoulders and the like) to inhibit unwanted fluids, debris, etc. from the passage 22. It is also to be appreciated that the various annular recesses 56 of the passage 22 can be further configured to securely and/or sealingly engage various medical devices for supplying and/or removing fluids, food, and/or medicines to or from the patient.

In addition or alternatively, the gastrostomic device 12 can further include a one-way valve 58 disposed within the hollow tube 20 for preventing a reflux of fluids out of the outer end 26 of the tube 20 from the deformable tip 28. However, the one-way valve 58 can permit the influx of fluids through the tube member 20 and past the one-way valve into the deformable tip 28. As shown, the one-way valve 58 can include a duckbill valve, though various other one-way valves 58 can also be used, such as a check valve or the like. The one-way valve 58 can be opened through an increase in pressure, such as through the introduction of a pressurized fluid, or can be opened mechanically through interaction with a portion of a feeding tube (not shown) or the like, though other methods can also be used. It is to be appreciated that the one-way valve 58 can be located at various positions within the longitudinal passage 22 for interaction with various feeding tubes and/or for various other performance reasons.

Further still, the gastrostomic device 12 can include a lock apparatus 60 being adapted to secure the gastrostomic device 12 to an insertion tool 14. The lock apparatus 60 can include a separate element attached to (e.g., adhesives, welding, fasteners, etc.) and/or formed with the gastrostomic device 12. Alternatively, the lock apparatus 60 can be integrally formed as a portion of the gastrostomic device 12, such as being formed in conjunction with the annular recesses 56. The lock apparatus can be disposed towards the outer end 26 of the hollow tube 22. In the shown example, the lock apparatus 60 can include the female portion of a bayonet connection (e.g., a twist and lock connection), though various other types of locking connections can also be used, such as a projection/detent, a snap connection, a tethered connection, etc.

Turning now the examples shown in FIG. 6-11, an insertion/removal device 14 is disclosed in accordance with another aspect of the invention. In one example, the insertion/removal device 14 can include a body 16, a stylus 62, and a trigger device 18, though various other elements can also be included. The insertion/removal device 14 can be utilized for insertion and/or removal of the gastrostomic device 12 though an opening in the wall of the abdomen and stomach or other viscera of a patient, such as an existing stoma. The body 16, stylus 62, and trigger device 18 can each include a generally rigid material, such a metal, plastic, hard rubber, or the like, though each can include various other materials as well.

As shown in FIGS. 6-9, the body 16 having an aperture 64 extending therethrough. The aperture 64 can extend completely through the body 16 from one end to the other, and can include a various cross-sectional geometries, such as a circular cross-section, through other geometries can also be used (e.g., triangular, square, polygonal, etc.). Additionally, the cross-sectional geometry can vary. For example, as shown in FIG. 9, a portion 66 of the cross-sectional geometry of the aperture 64 can taper from a relatively larger diameter to a relatively smaller diameter. Thus, as will be discussed more fully herein, the relatively larger diameter of the tapered portion 66 can facilitate insertion of the stylus 62 within the body 16, while the relatively smaller diameter can facilitate alignment and stabilization of the stylus 62 as it extends through and out of the aperture 64.

The body 16 can also include various other features. For example, the body 16 can include an attachment member 68 disposed at one end configured to removably attach the body 16 to a gastrostomic device, such as the device 12 discussed herein. The attachment member 68 can include a tubular, tapered portion 66 to facilitate attachment of the gastrostomic device 12 thereto. For example, the tubular, tapered portion 66 can be inserted into the outer end 26 of the gastrostomic device 12. The attachment between the gastrostomic device 12 and the body 16 can be maintained through various methods to inhibit inadvertent separation, including an interference fit, adhesives, fasteners, or even through a locking connection. Thus, the attachment member 68 of the body 16 can include a locking member 70 configured to removably secure the gastrostomic device 12 to the body 16. In the shown example, the attachment member 68 can include a projection, such as the male portion of a bayonet connection, for engagement with the female bayonet locking apparatus 60 previously discussed herein. Thus, to secure the gastrostomic device 12 to the body 16 of the insertion tool 14, the lock member 70 of the body 16 can be secured to the locking apparatus 60 of the gastrostomic device 12 though a twist-lock motion of a bayonet connection. It is to be appreciated that the locking member 70, and even the corresponding lock apparatus 60 of the gastrostomic device 12, can include various other configurations, such as a projection adapted to be received within a mating hole, or even a flange for secure engagement with a corresponding shoulder.

The body 16 can also include a handle portion 72 to facilitate manipulation of the insertion tool 14 by a user. As shown, the body 16 can include a pair of handle portions 72, each being configured to receive one of a pair of adjacent fingers of a user's hand while a central portion 74 of the body 16 is retained between the adjacent fingers. In addition or alternatively, the central portion 74 can further include one or more contoured finger grips 76 configured to help retain the user's fingers securely on the handles 72.

The body 16 can further include structure for selective operation and interaction with the trigger device 18, as will be discussed more fully herein. In one example, the central portion 74 of the body 16 can include a plurality of detents 78 (e.g., recessed portions) along its exterior surface, each detent being separated by a detent wall 80. The detents 78 can be arranged in various manners, such as in a linear pattern where each detent 78 is spaced a generally equal distance from an adjacent detent 78 along the central portion 74. Additionally, as shown in FIG. 9, the body 16 can include a pair of generally similar linear patterns of detents 78, each located on an opposite side of the body 16. Additionally, the detents 78 can each have the same or varying depths, and can even extend through the central portion 74 of the body. It is to be appreciated that various numbers of detents 78 arranged in various patterns, arrays, or even randomly can be utilized for interaction with the trigger device 18. In addition or alternatively, the body 16 can include positional indicia 82, such as the arrows shown and/or various words, numbers, or symbols (not shown), to indicate a measurement of the interaction between the body 16 and the trigger device 18.

Turning back briefly to the example shown in FIG. 1, the insertion and removal tool 14 can further include a retainer bracket 81 attached to the body 16. The retainer bracket 81 can be attached to the body 16 in various ways, and can even be removably attached. In the shown example, the retainer bracket 81 is removably and pivotally attached to the body by way of a pair of pivot arms 83 that are pivotally retained within opposing detents 78. The pivot arms 83 and pivotable connection permit the retainer bracket 81 to be rotated out of the way when it is not in use. The retainer bracket 81 further includes one or more retaining arms 85 configured to wrap about a portion of the gastrostomic device 12. In the shown example, the retainer bracket 81 has a generally "H"-shaped geometry and includes a pair of retaining arms 85 configured to wrap about the flat wings 48 of the gastrostomic device to retain and/or provide stability to the gastrostomic device 12 during insertion and/or removal thereof to a patient. In one example, the retainer bracket 81 can be utilized to reinforce a portion of the gastrostomic device 12 by transferring and/or spreading out a removal force applied by a user to the gastrostomic device 12 during removal thereof from a patient. It can be beneficial to provide such reinforcement when a gastrostomic device 12 has been attached to a patient for a relatively long period of time.

Turning now to the examples shown in FIGS. 10-11, an example stylus 62 and an example trigger device 18 are shown in accordance with an aspect of the present invention. The stylus 62 can include a generally tubular element having a proximal end 84 and a terminal end 86. As shown, the stylus 62 can be a generally solid object formed of a rigid material, such as plastic, metal, hard rubber, or the like, though it can also include a hollow interior portion (not shown). Additionally, the stylus 62 can have various cross-sectional geometries, such as circular, triangular, square, polygonal, etc. As shown, the stylus 62 includes a generally circular cross-sectional area that provides a curved terminal end 86. The proximal end 84 can be configured to be attached to a portion of the trigger device 18. In the shown example, the proximal end 84 can include screw threads 88 for threading into a central member 89 of the trigger device 18, though the attachment can also be made in various other manners, such as by adhesives, welding, fasteners, or even by being formed with the trigger device 18.

The terminal end 86 of the stylus 62 can be configured to extend a distance through the aperture 64 of the body 16. In the shown examples, the terminal end 86 is received within body 16 through the relatively larger diameter portion of the aperture 64, extends through the body 16, and extends from the body 16 through the relatively smaller diameter portion of the aperture 64. In operation, the terminal end 86 can be configured to extend a distance through the body 16 to deform a portion of a gastrostomic device 12 that is attached to the body 16. In one example, the terminal end 86 can be configured to apply an external force F to the apex 36 of the deformable tip 28 to thereby deform the deformable tip 28 to various configurations, such as between the first configuration to the second configuration, as discussed previously herein. Thus, depending upon the desired degree of deformation of the deformable tip 28, the terminal end 86 of the stylus 62 can be moved among various positions relative to the body 16.

Keeping with FIGS. 10-11, an example trigger device 18 is also shown. The trigger device 18 can further be adapted to selectively maintain a selected position of the terminal end 86 of the stylus 18 relative to the body without the use of an external force. Thus, for example, while an external force F can be applied to the gastrostomic device 12 for deformation of the deformable tip 28 through use of the stylus 62, the trigger device 18 can selectively maintain the position of the stylus 62, and the corresponding deformation of the deformable tip 28, without requiring the user to continuously apply the force F. As such, once the stylus 62 is set to a particular position relative to the body 16, the trigger device 18 can permit the user can freely manipulate the insertion device 14, along with the attached gastrostomic device 12 deformed to a desired configuration, without fear that the position of the stylus 62 or the configuration of the deformable tip 28 will inadvertently change.

As stated previously, the deformable tip 28 can be deformed to various configurations depending upon the desired cross-sectional area for a particular insertion and/or removal task. Thus, the trigger device 18 can be configured to maintain one of a plurality of positions of the stylus 62 relative to the body of the insertion tool 14. However, because accuracy is often of high importance in the performance of medical operations, it is to be appreciated that the trigger device 18 can be further configured to maintain a discrete position of the terminal end 86 of the stylus 62 relative to the body 16.

In one example, as shown in the various figures, the trigger device 18 can be adapted to selectively maintain a selected position of the terminal end 86 of the stylus 62 relative to the body 16 by way of a ratcheting mechanism. Though one example of a ratcheting mechanism is described herein, it is to be appreciated that various other configurations and types of ratcheting mechanisms can also be used. It is to be further appreciated that although a ratcheting mechanism is described herein, various other devices can be used to maintain a selected position of the terminal end 86 of the stylus 62 relative to the body without the use of an external force, such as, for example, a screw-down mechanism, a latching mechanism, a tie-down mechanism, a fastener mechanism, or the like.

For operation of the ratcheting mechanism, the trigger device 18 can include a projection 90 (e.g., a tooth or the like) configured to engage a selected detent 78 of the body 16. As shown in FIGS. 10-11, the projection 90 can be attached and/or formed with a ratchet arm 92 that is pivotally attached to the central member 89 of the trigger device 18 by a resilient pivot point 94. The resilient pivot point 94 can be constructed in various manners, including various mechanical pivot joints that can include various resilient elements, such as springs or the like. In the shown example, the resilient pivot point 94 can include a formed, resilient, jointed connection between the ratchet arm 92 and the central member 89 of the trigger device 18. The pivoted connection between the ratchet arm 92 and the pivot point 94 can act to permit the projection 90 to move towards and away from engagement with a selected detent 78 of the body 16. Thus, the trigger device 18 can further include a release arm 96 configured to release the projection 90 from engagement with a detent 78. As shown, because the release arm 96 is on one side of the pivot point 94, and the ratchet arm 92 is on the other, the pivot point 94 can act as a fulcrum for operation of the release arm 96. It is to be appreciated that although the shown example depicts a pair of ratchet arms 92 and release arms 94, the trigger device 18 can include various numbers of ratchet arms 92 and associated release arms 94 arranged in various manners.

In the shown example, the pivot point 94 can cause the ratchet arm 92 to resiliently bias the projection 90 towards engagement with a detent 78. Thus, when the trigger device 18 is engaged with the body 16 of the insertion tool 14, each projection can be caused to automatically engage an adjacent detent 78. Additionally, the projection 90 can include various geometries. In one example, as shown, the projection 90 can include a toothed structure having a ramped side 91 and a generally flat side 93. Thus, as the projection 90 automatically engages an adjacent detent 78 and is moved along the various detents 78 during positional adjustment, the ramped side 91 can be adapted to permit linear movement of the trigger device 18 relative to the body portion 16 in one direction. Correspondingly, the flat side 93 of the projection 90 can be adapted to inhibit reverse linear movement (e.g., motion in the opposite direction) by abutting the detent wall 80 of the detent 78 that the projection 90 is engaged with.

It is to be appreciated that during positional adjustment of the trigger device 18 relative to the body 16, the terminal end 86 of the stylus 62 can be engaging and resiliently deforming the deformable tip 28 of the gastrostomic device 12. As such, because the gastrostomic device 12 can include a resilient silicone material, an increasing deformation from the applied external force F can result in an increasing, generally equal and opposite force transmitted back to the trigger device 18. However, the aforementioned equal and opposite force can be resisted by abutment of the flat side 93 of the projection against a detent wall 80 to inhibit reverse movement of the trigger device 18 and stylus 62, and to maintain of a desired configuration of the deformable tip 28. Thus, the geometry of the projection 90 can permit one-way, ratcheted movement of the trigger device 18 relative to the body 16. Additionally, to release the projection 90 from engagement with a detent 78, a user can apply a force to the release arm 96 to pivot the ratchet arm 92 away from the body 16 of the insertion tool 14 to thereby release the projection 90. Subsequently, the aforementioned generally equal and opposite force from the deformation of the silicone can cause the trigger device 18 and stylus 62 to be moved away and released from the body 16.

The trigger device 18 can also include various other elements. For example, the trigger device 18 can include a plunger member 98 disposed at one end and configured to be actuated by the hand of a user for selectively positioning the terminal end 86 of the stylus 62 relative to the body 16 of the insertion device 14. In one example operation to cause positional adjustment of the trigger device 18 and stylus 62 relative to the body 16, a user can place a pair of fingers, such as the index finger and middle finger, each on one of the handles 72 of the body 16, and a thumb on the plunger member 98. The user can then use the thumb to apply the external force F through the plunger member 98 and to the stylus 62 for deformation of the deformable tip 28. It is to be appreciated that various other configurations of a plunger member 98 can also be used that can engage other portions of a user, such as other portions of a user's hand (e.g., other fingers, palm, etc.). In addition or alternatively, the ratchet arms 92 can cooperate with positional indicia 82 of the body 16 to indicate and/or measure the selected position of the terminal end of the stylus 62 relative to the body 16. In one example, the ratchet arms 92 can include various indicia (e.g., words, numbers, symbols, not shown) and/or positional markers (dash marks or the like, not shown) that can be compared against the position indicia of the body 16.

Turning now to the examples schematically shown in FIGS. 12a-12g, an example method of inserting a gastrostomic device for insertion through an opening in the wall of the abdomen and stomach (e.g., an existing stoma), or other viscera of a patient (e.g., bladder, chest, colon, etc.) will now be described. It is to be appreciated that although the following description utilizes the gastrostomic device 12 previously described herein, the method can be utilized with various other gastrostomic devices or the like, including similar devices that can be utilized in various other medical procedures (e.g., urinary bladder drainage, ileostomy, jejunostomy, cystostomy, or the like). Additionally, the method can also include more or less various other steps. Further, it is to be appreciated that the example method is shown only schematically in the various figures, and as such the various elements shown in the figures are not necessarily drawn to scale.

Beginning with the example shown in FIG. 12a, the method includes the step of providing a gastrostomic device for insertion into a patient, such as the gastrostomic device 12 discussed previously herein. Next, an insertion device is provided, such as the insertion device 14 including the body 16, stylus 62, and trigger device 18 discussed previously herein, for inserting the gastrostomic device 12 into the patient. Next, as shown in FIG. 12a, the insertion device 14 is attached to the outer end 26 of the gastrostomic device 12 along the direction indicated by arrow A. In one example, the attachment member 68 of the body 16 can be inserted into the outer end 26 of the gastrostomic device 12 and can be removably attached thereto as discussed herein, such as through engagement of the lock apparatus 60 with the locking member 70. Subsequently, the terminal end 86 of the stylus 62 can be inserted into the longitudinal passage 22 of the tube member 20 until the terminal end 86 of the stylus 62 is adjacent to and/or in contact with a portion of the deformable tip 28. In another example, the terminal end 86 of the stylus 62 can be first inserted into the longitudinal passage 22 of the tube member 20 until the attachment member 68 of the body 16 is inserted into the outer end 26 of the gastrostomic device 12. At this point, the terminal end 86 of the stylus 62 may be adjacent to and/or in contact with a portion of the deformable tip 28 of the gastrostomic device 12. Indeed, the terminal end 86 can be in contact with the apex 36 and could cause some deformation of the deformable tip 28.

Next, as shown in FIG. 12b, the insertion device 14 can be removably attached to the gastrostomic device 12. Specifically, the insertion device 14 is attached in a secure manner that can inhibit inadvertent separation of the gastrostomic device 12. As previously discussed, the attachment can be performed in various manners. In the shown example, the locking member 70 of the insertion device 14 is inserted into the lock apparatus 60 of the gastrostomic device 12 and is secured thereby by way of a twist-lock operation (e.g., arrow B) representative of a bayonet connection. It is to be appreciated that the twist-lock operation can include various amounts of rotation, such as 90°, 180°, 270°, or other angle.

Next, as shown in FIG. 12c, the insertion device 14 is utilized to deform the enlarged tip 28 of the gastrostomic device 12 into a desired configuration associated with a desired cross-sectional area of the tip 28, such as the second configuration previously discussed. For example, as shown in FIG. 12b, the tip 28 has a cross-sectional area $X_1$ corresponding to the first configuration, while in FIG. 12c, the tip 28 has a relatively smaller cross-sectional area $X_2$ corresponding to the second configuration. It is to be appreciated that the insertion device 14 can be used to deform the tip 28 into any of various cross-sectional areas corresponding to that required by a particular patient, such as may be required for insertion into a stoma of a patient having a particular size.

As discussed previously, the deformable tip 28 can be deformed by extending the stylus 62 a distance through the body 16 to have the stylus 62 act upon the apex 36 of the tip 28. Thus, a user can move trigger member 18 in the direction indicated by arrow C, such as by use of the plunger member 98. At the same time, the ratcheting mechanism including the interaction of the projections 90 with the detents 78 can act to maintain a selected position of the terminal end 86 without the use of an external force. Thus, a user can be permitted greater freedom to manipulate the assembly (e.g., especially during the placement and articulation of the device through the stoma 104 site depicted in FIGS. 12e and 12f) without having to be concerned about having to manually maintain the desired, extended deformation of the tip 28. Further, the user can utilize the positional indicia 82 of the body 16 to measure the relative positioning of the trigger member 18 relative to the body 16, permitting an increased accuracy and repeatability in usage.

In addition, it is to be appreciated that deformation of the tip 28, in cooperation with the action of the straps 40 and reduced thickness end wall portions 42, acts to deform the tip 28 into a more streamlined shape for insertion and/or removal from a patient. Thus, deformation of the tip 28 serves to both correspond the cross-sectional area $X_2$ of the tip 28 to more closely match the size of the patient's stoma, and provides a more streamlined shape to facilitate insertion and/or removal of the gastrostomic device 12. It is to be further appreciated that deformation of the tip 28 can also cause deformation of the hollow tube 20, such as a stretching that can elongate the tube 20 while also reducing its diameter.

Figure 12D:
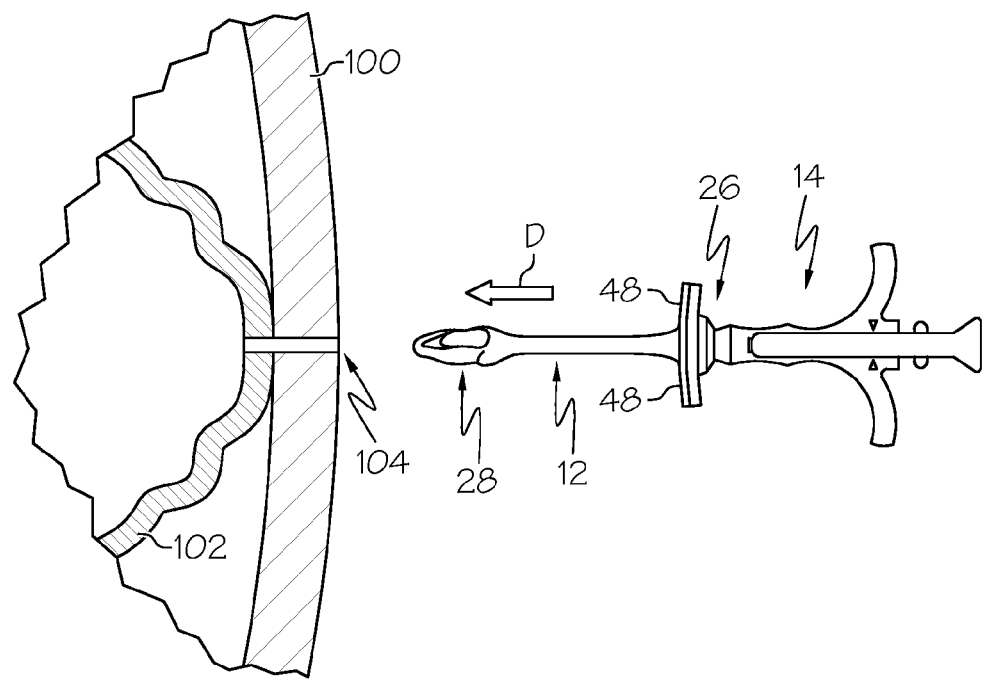

Next, as shown in FIG. 12d, the insertion and removal device 14 can be used to insert the deformable tip 28 of the gastrostomic device 12 into the patient along the direction shown by arrow D. In the shown example, the deformable tip 28 can be inserted through a stoma 104 or the like through the wall of the abdomen 100 and into the stomach 102 or other viscera of a patient. As discussed previously, it is to be appreciated that the deformable tip 28 can be inserted into various other viscera or organs of a patient, such as a bladder, chest, colon, etc.

Figure 12E:
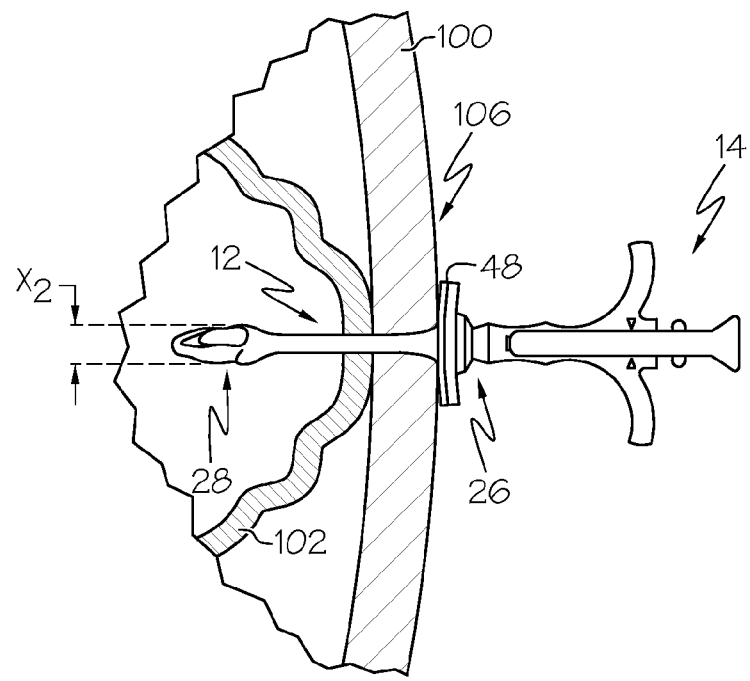

Next, as shown in FIG. 12*e*, the deformable tip 28 of the gastrostomic device 12 is inserted into the stomach 102 until the outer end 26 of the gastrostomic device 12 is adjacent the abdomen 100 of the patient. Specifically, in the shown example, the gastrostomic device 12 is inserted into the stomach 102 of the patient until the wings 48 of the outer end 26 are adjacent to and/or abut the outer surface 106 of the abdomen 100.

Figure 12F:
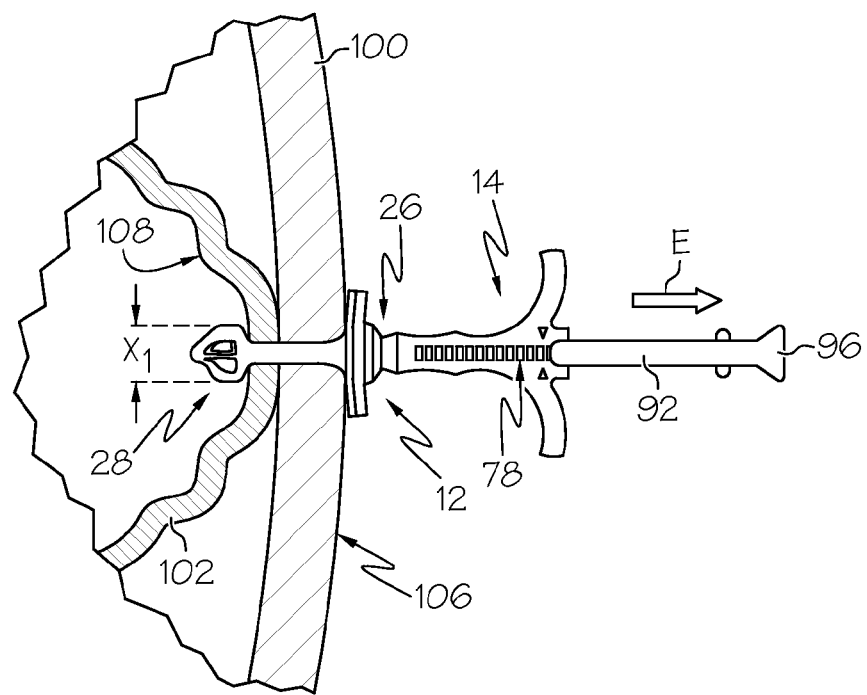

Next, as shown in FIG. 12*f*, the insertion tool 14 is utilized to permit the deformable tip 28 to resiliently return to the first configuration (e.g., having a first cross-sectional area $X_1$). In one example, as previously discussed, the release arm 96 of the trigger device 18 can be actuated to pivot the ratchet arm 92 and thereby release the projections 90 from the detents 78. Additionally, the stretched, resilient material of the gastrostomic device 12 can provide a counter force to urge the trigger device 14 in the direction of arrow E to facilitate this process. Once the force supplied by the terminal end 86 of the stylus is removed, the deformable tip 28 can return to the first configuration (e.g., having the first cross-sectional area $X_1$) and expand against the inner wall 108 of the stomach 102. The outer diameter of the hollow tube 20 can also return generally to its original diameter within the stoma 104. It is to be appreciated that the first cross-sectional area $X_1$ can be greater than that of the stoma 104 to inhibit inadvertent removal of the gastrostomic device 12 from the patient. Thus, the flat wings 48 abutting the outer surface 106 of the abdomen 100, along with the deformable tip 28 abutting the inner wall 108 of the stomach 102, make the device self-retaining in the patient.

Figure 12G:
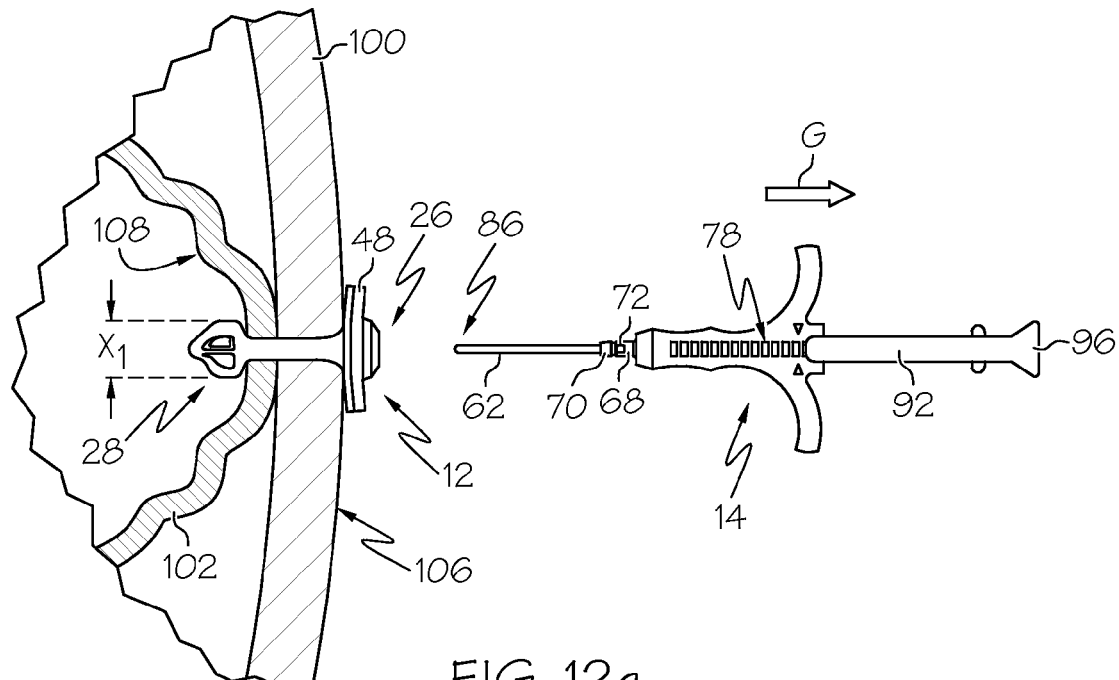

Next, as shown in FIG. 12*g*, the insertion device 14 can be detached from the outer end 26 of the gastrostomic device 12. The locking member 70 can be unsecured from the lock apparatus 60 through a reversal of the twist-lock operation (e.g., bayonet connection), and the attachment member 68 can be removed from the outer end 26 of the gastrostomic device 26. Next, terminal end 86 of the stylus 62 is removed from the hollow tube 20 as the insertion device 14 is moved away from the gastrostomic device 12 along the direction of arrow G. Finally, a medical device (e.g., a feeding or medicine delivery/extraction device, not shown) can be connected to the gastrostomic device 12 to deliver fluids or the like to the stomach 102 through the various apertures 28 of the gastrostomic device 12, or if desired, the plug 50 can be inserted into the outer end 26 to protect the passage 22.

It is to be appreciated that the method heretofore described in association with an insertion procedure for the gastrostomic device 12 is similar to a procedure for subsequent removal of the device 12 from a patient. Similar steps can be followed, though in a reverse order, to remove the device 12. It is to be further appreciated that an additional benefit of the insertion and removal device 14 is the ability to blindly deform the deformable tip 28 of the gastrostomic device 12 while it is located within the stomach 102 of the patient. In conjunction with the ratcheting mechanism and the positional indicia 82 of the body 16, the insertion and removal tool 14 can permit an increased accuracy and repeatability in usage when inserting and/or removing the gastrostomic device 12, even in situations where the user is unable to directly view the deformable tip 28.

Turning now to the examples shown in FIGS. 13*a* and 13*b*, an example method of forming the gastrostomic device 12 will now be described. It is to be appreciated that although the following description utilizes the gastrostomic device 12 previously described herein, the method can be utilized with various other gastrostomic devices or the like, including similar devices or even other devices including different structure, that can be utilized in various other medical procedures (e.g., urinary bladder drainage, ileostomy, jejunostomy, cystostomy, or the like). Additionally, it is to be appreciated that the method can also include more or less other steps.

Figure 13A:
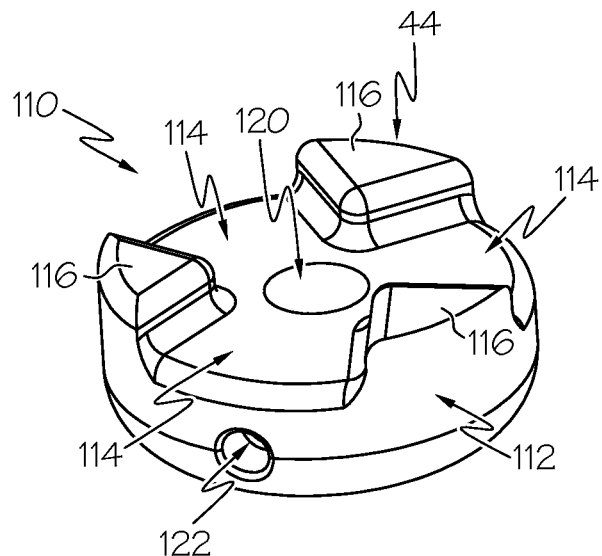
FIG. 13a illustrates a perspective view of an example core in accordance with an aspect of the present invention.

Beginning with the example shown in FIG. 13*a*, the method includes the step of providing a core 110 having a geometry generally equal to an interior geometry of a hollow enlarged tip 28 of the gastrostomic device 12. That is, the overall geometry of the core 110 can be generally equal to (e.g., a negative of) the hollow interior 30 geometry of the enlarged tip 28. Thus, as shown, the core 110 can include an annular exterior surface 112 that can form the interior surface of the outer cap portion 34. The core 110 can also include recessed portions 114 and raised portions 116 configured to cooperatively form the end wall 32. The recessed and raised portions 114, 116 can include various geometries, such as the triangular geometry 44 of the raised portions 116. As stated previously herein, the end wall 32 can include both a relatively thicker portion (e.g., thickness $T_1$) and a relatively thinner portion 42 (e.g., thickness $T_2$). As can be appreciated, the recessed portions 114 of the core 110 can act to form the relatively thicker portions, while the raised portions 116 can act form the relatively thinner portions 42 of the end wall 32. It is to be appreciated that the geometrical difference $T_3$ in height between the recessed portions 114 and the raised portions 116 corresponds to the difference in thickness between the relatively thicker and thinner portions $T_1$, $T_2$ of the end wall 32. It is further to be appreciated that although there are three recessed portions 114 and three raised portions 116 shown, various numbers of raised and recessed portions can be included and arranged in various manners as desired. Indeed, the core 110 could include a plurality of raised and recessed portions having various different geometries.

Figure 13B:
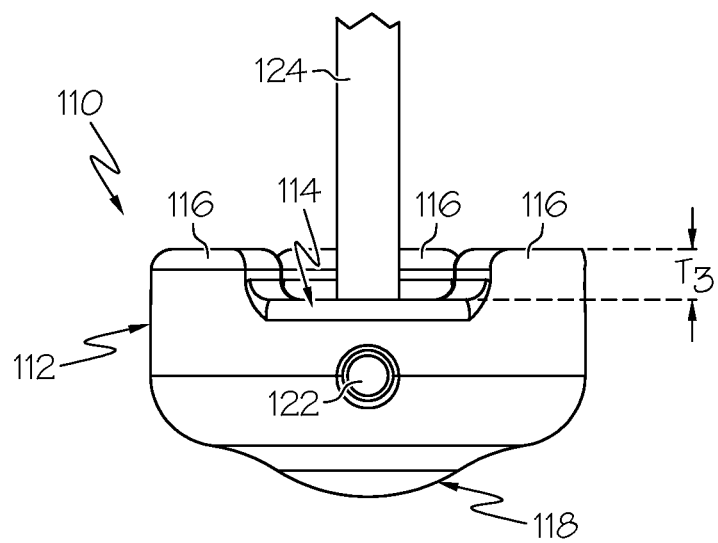
FIG. 13b is similar to FIG. 13a, but shows a front view of the core.

Turning to FIG. 13*b*, the core 110 can also provide for other features of the hollow interior 30 of the enlarged tip 28. For example, the core 110 can also include an apex portion 118 configured to form the contour of the apex 36. The apex portion 118 can include the sloping geometry shown in order to facilitate focusing the external force F of the terminal end 86 of the stylus 62 towards the thicker apex 36 of the enlarged tip 28 to maximize the strength of the tip 28. It is to be appreciated that the apex portion 118 can also include various other geometries for various other purposes. Indeed, the core 110 can also include various other features as may be desired in for the enlarged tip 28.

Subsequent to the step of providing the core 110, the gastrostomic device 12 can be formed around the core 110. The gastrostomic device 12 can be formed using various methods, such as molding, stamping, cold or hot working, casting, etc. In one example, where the gastrostomic device 12 includes an elastomeric material, such as medical grade silicone, the device 12 can be formed using an injection molding operation. Thus, the silicone can be injection molded around the core 110 to form the gastrostomic device 12, while the core 110 will inhibit silicone from forming within the hollow interior area 30 of the enlarged tip 28.

It is to be appreciated that in such a molding operation, the core 110 can be placed within an external mold (not shown) to constrain and/or define the molding of the exterior features of the gastrostomic device 12. For example, during the molding operation, the external mold (not shown) can be configured to form the aperture 38 through the outer cap portion 34 of the enlarged tip 28. In addition or alternatively, the molding operation can be adapted to form the strap 40 disposed within the aperture 38, and can cooperate with the core 110 to attach the strap 40 to a portion of the end wall 32 and to the relatively thinner portion 42 of the outer cap portion 34.

Subsequent to the step of forming the gastrostomic device 12 around the core 110, the method can further include the step of disposing of the core 110 from the gastrostomic device 12 to thereby form the hollow interior 30 of the enlarged tip 28. The core 110 can be disposed from the gastrostomic device 12 in various manners. In one example, the core 110 can be removed from the hollow interior 30 and discarded, such as being removed through one of the apertures 38.

In another example, the core 110 can be disposed of by dissolving the core 110 while it is still disposed within the hollow interior 38. It is to be appreciated that the step of dissolving the core 110 can be accomplished using various methods that are capable of altering the structure of the core 110 from a solid to a liquid, solid/liquid mixture, and/or gas that can facilitate removal of the core 110. For example, where the core 110 is formed of a dissolvable thermoplastic material or the like, it can be dissolved using a heating operation. Thus, the core 110, or even the gastrostomic device 12 as a whole, can be heated to a temperature that is greater than the melting point of the thermoplastic core 110 (e.g., 400° F. or other suitable temperature), but less than a temperature that will cause damage to or degradation of the material (e.g., silicone) of the gastrostomic device 12. In yet another example, the core 110 can be dissolved through application of a chemical to the core 110. In one example, water having particular properties (e.g., pH, alkalinity, temperature, etc.) can be used to dissolve the core 110, though it is to be appreciated that various chemicals can be used depending upon the particular material properties of the core 110.

After the core 110 is dissolved, the remaining material can be removed from the hollow interior 30 of the enlarged tip 28 in various manners. In one example, the material can exit the enlarged tip 28 through the various apertures 38 formed therein. In another example, the dissolved core material can be removed through the longitudinal passage 22 of the hollow tube 20, such as by way of a vacuum operation.

The formation of the gastrostomic device 12 utilizing the core 110 can further include various other features and/or steps. In one example, the gastrostomic device 12 can be formed using a plurality of cores. As shown in FIG. 13b, the core 110 (e.g., a first core) can be removably or non-removably attached to a second core 124. The second core 124 can be used to form additional features of the gastrostomic device 12, such as additional features of the hollow interior 30 (e.g., the annular recesses 56, the one-way valve 58, the lock apparatus 60, etc.). The first core can be attached to the second core 124 in various manners, such as an adhesives, welding, interference fit, fasteners, or they can even be formed together as a single core. In the shown example, the second core 124 is attached to the first core 110 by an interference fit and is adapted to form the interior geometry of the longitudinal passage 22 of the hollow tube 20, including either or both of the annular recesses 56 and the one-way valve 58. Thus, the second core 124 has a tubular geometry that is configured to be received within (e.g., press fit) a central hole 120 of the first core 110.

As such, during the formation process, such as injection molding, the gastrostomic device 12 is formed around both the first and second cores 110, 124. After the gastrostomic device 12 is formed, both of the cores 110, 124 can be removed from the interior of the device 12 in various manners. In one example, either or both of the cores 110, 124 can be removed and disposed of. In another example, either or both of the cores 110, 124 can be dissolved out of the hollow interiors 38, 22. In the shown example, the first core 110 can be formed of a dissolvable material, while the second core 124 can be formed of a non-dissolvable material, such as metal or the like. Thus, the first core 110 can be removed through a dissolving process, while the second core 124 can be removed, and possibly reused, through the outer end 26 of the formed gastrostomic device 12.

In addition or alternatively, where a molding operation is used, the core 110 can include structure to facilitate and maintain alignment and/or orientation of the core 110 within the external mold (not shown) during the molding process. In one example, the core 110 can include an alignment hole 122 through a side of the annular exterior surface 112. Thus, when the core 110 is placed within the external mold, an alignment pin (not shown) can be attached to the external mold can be inserted into the alignment hole 122 of the core 110 to thereby align and retain the core 110. It is to be appreciated that usage of such an alignment pin can result in a corresponding hole 126 being formed though a portion of the outer end cap 34 of the deformable tip 28, though other methods can also be used to avoid the formation of such a hole 126. It is to be further appreciated that various other methods can further be used to align and maintain the core 110 during a molding operation, and such other methods are considered to be within the scope of the invention.

The invention has been described with reference to various example embodiments. Obviously, modifications and alterations will occur to others upon a reading and understanding of this specification. It is intended to include all such modifications and alterations insofar as they come within the scope of the appended claims or the equivalents thereof.

What is claimed is:

1. A device for inserting a non-balloon gastrostomic device through an opening in the wall of the abdomen and stomach or other viscera of a patient, the device comprising:
   a body including a tapered aperture extending therethrough, with the body substantially enclosing the aperture and the aperture having a larger opening at one end than the other, with the body having a plurality of detents along its exterior surface and having an attachment member positioned at one end of the body configured to removably fix the body to an opening in a gastrostomic device;
   a stylus having a proximal end and a terminal end, the terminal end being configured to extend a distance through the aperture of the body to deform a portion of a gastrostomic device fixed to the body; and
   a trigger device attached to the proximal end of the stylus and being adapted to selectively maintain a selected position of the terminal end of the stylus relative to the body without the use of an external force, the trigger device including at least one projection, with the projection being configured to engage one of the plurality of detents;
   at least one ratchet arm attached to the trigger device to permit the at least one projection to move towards and away from engagement with the plurality of detents;
   at least one release arm configured to release the at least one projection from engagement with the plurality of detents.

2. The device of claim 1, wherein the attachment member is a locking member having a locking feature for removably mating with an opening of a gastrostomic device and a tapered end for insertion into the opening of the device, with the tapered end serving to open a valve disposed in the gastrostomic device.

3. The device of claim 1, wherein the body further comprises a handle portion.

4. The device of claim 1, wherein the body further comprises positional indicia configured to indicate the selected position of the terminal end of the stylus relative to the body.

5. The device of claim 1, wherein the body further comprises a retainer bracket configured to reinforce a portion of a gastrostomic device during removal thereof from a patient.

6. The device of claim 5, wherein the retainer bracket is removably and pivotally attached to the body by a pair of pivot arms that are pivotally retained within opposing detents on the body.

7. The device of claim 1, further comprising a gastrostomic device that includes a deformable tip having an apex, the apex including a thickened portion configured to withstand application of an external force without damage or degradation of the gastrostomic device.

8. The device of claim 1, wherein the trigger device further comprises a plunger member disposed at one end of the trigger device and configured to be actuated by a hand of a user for selectively positioning the stylus relative to the body.

9. A device for inserting a non-balloon gastrostomic device through an opening in the wall of the abdomen and stomach or other viscera of a patient, the device comprising:
   a body including an aperture extending therethrough and a plurality of detents along its exterior surface and an attachment member configured to removably attach the body to a gastrostomic device, with the attachment member having a locking feature for locking a gastrostomic device to the body and a tapered end for insertion into an opening in the device, with the tapered end serving to open a valve within the device;
   a stylus having a proximal end and a terminal end, the terminal end being configured to extend a distance through the aperture of the body to deform a portion of a gastrostomic device attached to the body; and
   a trigger device attached to the proximal end of the stylus at a connection portion and being adapted to selectively maintain a selected position of the terminal end of the stylus relative to the body without the use of an external force, the trigger device further comprising at least one mating feature for engaging one of the plurality of detents; and
   a release mechanism for releasing the mating feature from the plurality of detents.

10. The device of claim 9, wherein the mating feature comprises at least one ratchet arm having an projection extending therefrom at one end thereof, said ratchet arm is coupled to the trigger device such that the projection moves towards and away from engagement with one of the plurality of detents; and
   the release feature comprises at least one release arm configured to release the projection from engagement with one of the plurality of detents.

11. The device of claim 10, wherein the at least one ratchet arm is coupled to the connection portion and the at least one release arm is connected to the connection portion of the trigger device.

12. The device of claim 11, wherein the at least one ratchet arm is longitudinally aligned with the at least one release arm.

13. An apparatus for inserting a non-balloon gastrostomic device having a hollow interior and a deformable tip through an opening in a patient's body, comprising:
   a body having a wall defining a channel-like guiding aperture extending therethrough, with the wall of the body substantially surrounding the aperture and having a plurality of detents defined along at least a portion of the length of the wall, said body having an attachment portion for removably coupling with a hollow interior of a gastrostomic device; and
   a trigger device coupled to the body at one end of the trigger device and having a connection portion defined at the other end of the trigger device, with a stylus coupled to the connection portion of the trigger device and extending into the guiding aperture of the body, with the trigger device including a member having at least one projection for engaging one or more of the plurality of detents, wherein the trigger device selectively maintains a discrete position of the stylus relative to the body.

14. The apparatus of claim 13, wherein the member having at least one projection is an arm coupled to the connection portion of the trigger device, said arm holding the projection at an end thereof.

15. The apparatus of claim 14, wherein the arm includes a ratchet portion that extends in one direction relative to the connection portion and a release portion that extends in an opposite direction relative to the connection portion, with the ratchet portion of the arm being longitudinally aligned with the release portion of the arm; and
   the ratchet portion of the arm includes the at least one projection.

16. The apparatus of claim 13, wherein the attachment portion includes a locking feature for locking the end of the body to an opening in a gastrostomic device.

17. The apparatus of claim 16, wherein the locking feature includes a tapered portion for insertion into an opening in a gastrostomic device, with the tapered portion having a configuration for opening a valve positioned in the gastrostomic device.

18. The apparatus of claim 13, wherein the aperture in the body tapers from a larger diameter at one end to a smaller diameter at the other end, with the smaller diameter being at the attachment portion end of the body.

19. The apparatus of claim 13, further comprising a plunger coupled to the trigger device for actuation of the trigger device by a hand of a user to selectively position the stylus relative to the body.

20. The apparatus of claim 13, wherein the arm comprises a pair of arms that include a ratchet portion that holds a projection and a release portion that is configured to release the projection of each ratchet portion from a corresponding detent.

* * * * *